(12) United States Patent
Abe et al.

(10) Patent No.: US 6,540,671 B1
(45) Date of Patent: Apr. 1, 2003

(54) ELECTRONIC ENDOSCOPE APPARATUS DRIVING LIGHT SHIELDING PLATE

(75) Inventors: Kazunori Abe, Saitama (JP); Fujio Okada, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 10/237,062

(22) Filed: Sep. 9, 2002

(30) Foreign Application Priority Data

Sep. 21, 2001 (JP) ........................................ 2001-288183

(51) Int. Cl.$^7$ ................................................. A61B 1/06
(52) U.S. Cl. ...................... 600/180; 600/181; 362/574; 348/68
(58) Field of Search .................... 348/22, 23, 220.1, 348/221.1, 68–70; 600/109, 160, 178, 180, 181; 362/574

(56) References Cited

U.S. PATENT DOCUMENTS

| 6,002,425 | A | * | 12/1999 | Yamanaka et al. | ............ | 348/68 |
| 6,254,531 | B1 | * | 7/2001 | Higuchi et al. | ............ | 600/178 |
| 6,413,207 | B1 | * | 7/2002 | Minami | ...................... | 600/109 |

* cited by examiner

*Primary Examiner*—John Mulcahy
(74) *Attorney, Agent, or Firm*—Snider & Associates; Ronald R. Snider

(57) ABSTRACT

There is provided a light shielding plate to shield light from a light source lamp, and this light shielding plate is rotated and driven by a light shielding plate drive circuit, and a charge stored in a CCD for a period of, for example, 20H at a start of an effective period J of a vertical scanning period, is discharged and this is set as a non-operating period and a drive control over the light shielding plate for a period of 40.5H which is a sum of this non-operating period and a blanking period B (20.5H) is performed. This provides an adequate margin of time for controlling the light shielding plate at starting and stopping times and makes the drive control easier.

3 Claims, 3 Drawing Sheets

FIG. 3
PRIOR ART
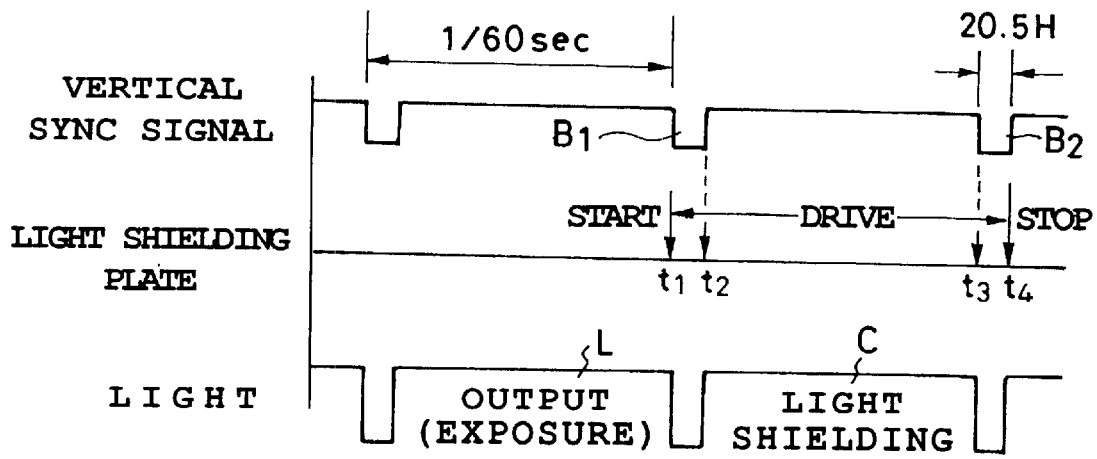
FIG. 4
PRIOR ART
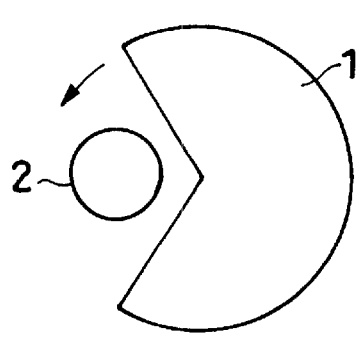
FIG. 4(A) START
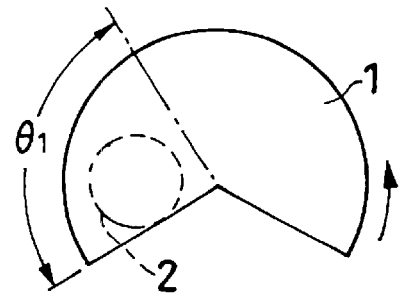
FIG. 4(B)
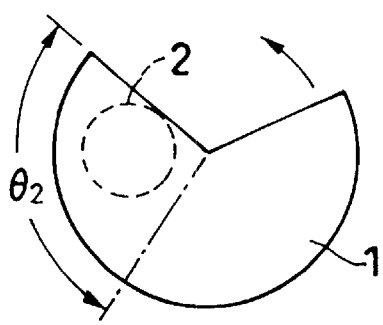
FIG. 4(C)
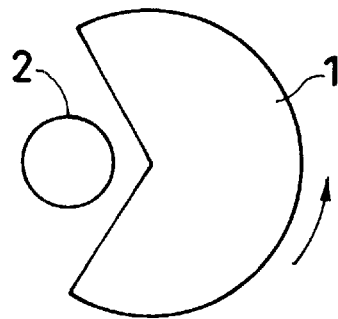
FIG. 4(D) STOP

ELECTRONIC ENDOSCOPE APPARATUS DRIVING LIGHT SHIELDING PLATE

BACKGROUND OF THE INVENTION

This application claims the priority of Japanese Patent Application No. 2001-288183 filed on Sep. 21, 2001 which is incorporated herein by reference.

1. Field of the Invention

The present invention relates to an electronic endoscope apparatus, and more particularly, to contents of control of an electronic endoscope apparatus which is capable of reading stored charge obtained through one exposure by an image pickup element as 1-frame all pixel signals using a light shielding period set by a light shielding plate.

2. Description of the Related Art

In an electronic endoscope apparatus, light from a light source lamp is guided through a light guide to a tip of a scope and the light is irradiated from this scope tip onto an object under observation and an image of this object is captured by an image pickup element such as a CCD (Charge Coupled Device) via an objective optical system. This CCD reads signals (charge) stored every 1-field period one by one and forms a moving image. On the other hand, when a still image is formed, the CCD reads signals of all pixels obtained through exposure for 1 vertical scanning period taking advantage of a light shielding period.

FIG. 3 illustrates a light shielding plate drive period when the above-described still image is formed and the electronic endoscope apparatus uses a vertical sync signal of a ⅟60 sec period shown at the top of FIG. 3, for example. On the other hand, when a still image is formed, the light shielding plate is driven during a drive period which consists of a 1 vertical scanning period plus a 20.5H (H: horizontal scanning period) vertical blanking period as shown in the middle of FIG. 3, and in this way a light shielding period C is set as shown in the bottom of FIG. 3.

Then, during a light output period (exposure period) L at the bottom of FIG. 3, odd field signals in all pixel signals stored in the CCD are read during the above-described light shielding period C and even field signals are read during the next vertical scanning period of the light shielding period C, and in this way a still image is formed. According to this all pixel reading system, a still image is displayed on a monitor using all pixel signals obtained through exposure within a 1 vertical scanning period, and therefore this system has an advantage of obtaining clearer images without being affected by motions of an object under observation than when a moving image is formed.

However, since the conventional electronic endoscope apparatus needs to complete an operation from the start to stop of the above-described light shielding plate within a 1 vertical scanning period +20.5H, there is a problem that drive control over the light shielding plate is complicated.

FIGS. 4(A) to 4(D) show an operation from the start to stop of a rotating light shielding plate, and as shown in FIG. 4(A), a light shielding plate 1 is set in a position that will not block light source light (light path) 2 during the formation of a moving image. On the other hand, during the formation of a still image, once the light shielding plate 1 starts to rotate from this position, the light source light 2 can be completely shielded when the light shielding plate 1 moves to the position in FIG. 4(B) by an angle $\theta_1$. On the other hand, when the light shielding plate is stopped, the light source light 2 can be completely shielded up to the position in FIG. 4(C) and the light source light cannot be completely shielded from this position to the position in FIG. 4(D), that is, the range of $\theta_2$.

Furthermore, the start of the above-described rotating light shielding plate 1 is controlled for a short blanking period $B_1$ ($t_1$ to $t_2$) of 20.5H (approximately 1.3 msec) shown in FIG. 3 and rotating the light shielding plate by the above-described angle 61 to completely shield the light source light during this period requires the torque for starting a motor that drives the rotation of the light shielding plate 1 to be increased. On the other hand, the stop of the light shielding plate 1 is also controlled for a short blanking period $B_2$ ($t_3$ to $t_4$) of 20.5H and rotating the light shielding plate by the above-described angle $\theta_2$ to completely stop the light shielding plate during this period requires brake control, etc. to give the motor a reverse potential. Thus, there is inconvenience that not only control of the light shielding plate 1 at the time of start and stop is complicated but also the circuit configuration is complicated.

SUMMARY OF THE INVENTION

The present invention has been achieved in view of the problems described above and it is an object of the present invention to provide an electronic endoscope apparatus capable of securing a control time at the time of starting and stopping the light shielding plate within an effective period of the vertical scanning period and driving the light shielding plate easily and with a simple circuit configuration.

In order to attain the above object, the present invention provides an electronic endoscope apparatus including an image pickup element that captures an image of an object under observation illuminated by light source light and a light shielding plate to shield the light source light, and capable of reading all pixel signals of the image pickup element taking advantage-of a period during which the light source light is shielded by this light shielding plate, characterized by including an image pickup element drive circuit that discharges the charge stored by the image pickup element during a predetermined period within an effective period after a blanking period of a vertical scanning period (during which image data can be retained) and performs control so as to set a non-operating period, and a light shielding plate drive circuit that performs drive control over the light shielding plate during a period including the non-operating period set by this image pickup element drive circuit.

Furthermore, another invention is characterized by reading, when a moving image is formed, charge stored from the image pickup element every 1 vertical scanning period as field signals without driving the light shielding plate and driving, when a still image is formed, the light shielding plate to read all pixels obtained through exposure within the 1 vertical scanning period as frame signals.

Furthermore, another invention performs electronic shutter control for controlling the charge storage time as a shutter speed after the control of the non-operating period and can thereby control the exposure time.

The above-described configuration provides a non-operating period within an effective period of the 1 vertical scanning period through discharge control over the stored charge of the image pickup element in the form of linking the non-operating period with a vertical blanking period. For example, if this non-operating period is set to 20H, it is possible to use a total period of 40.5H which is 20H plus a blanking period as the time to drive the light shielding plate both at the starting and stopping times. This gives an adequate margin of time for controlling the start and stop of the light shielding plate when all pixels are read and makes it easier to provide a completely shielded state and also simplifies the configuration for this purpose, too.

BRIEF DESCRIPTION OF THE DRAWINGS

FIG. 3 illustrates waveform charts showing operations or actions of various sections when a conventional light shielding plate is driven; and FIGS. 4(A) to 4(D) illustrate operation states from start to stop of the light shielding plate used by an electronic endoscope apparatus.

DETAILED DESCRIPTION OF THE PREFERRED EMBODIMENTS

Figure 1:
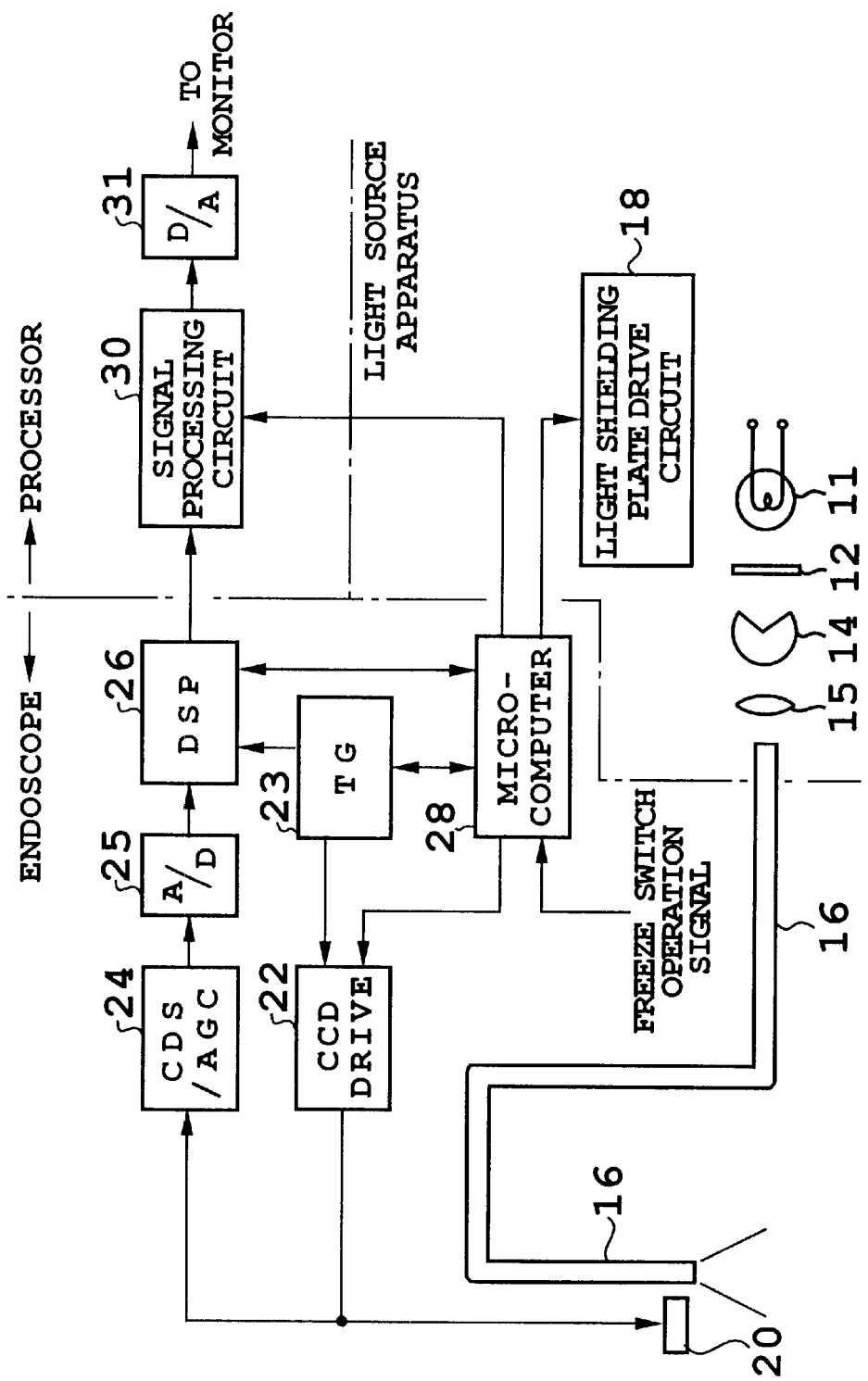
FIG. 1 is a block diagram showing a main configuration of an electronic endoscope apparatus according to an embodiment of the present invention.

FIG. 1 shows part of a configuration of an electronic endoscope apparatus according to an embodiment of the present invention and this electronic endoscope apparatus is provided with a scope, a processor and a light source apparatus, etc. In FIG. 1, the light source apparatus is provided with a light source lamp 11 such as a xenon lamp, a light quantity adjuster 12, a light shielding plate 14 that rotates to shield light from the lamp 11 and a condensing lens 15, and light from this condensing lens 15 is supplied to a light guide 16. The light shielding plate 14 is connected to a light shielding plate drive circuit 18 and the light shielding plate drive circuit 18 of this embodiment controls the rotation of a motor when a still image is formed and rotates the light shielding plate 14 a turn. Instead of this light shielding plate 14, it is also possible to use anything that is driven by swinging motion or linear motion, etc. other than rotational motion.

The light guide 16 is led from the light source apparatus to the scope tip and a CCD (image pickup element) 20 for capturing an image of an object under observation is placed at this scope tip via an objective optical system. This CCD 20 is connected to a CCD drive circuit 22 and this CCD drive circuit 22 forms discharging pulses (SUB pulses) and reading pulses based on timing signals such as a clock signal, vertical sync signal and horizontal sync signal supplied from a timing generator (TG) 23 and controls the reading of charge stored in the CCD 20. This embodiment controls brightness of an image through the light quantity adjuster 12, but it is also possible to keep the brightness of an image constant by variably controlling the exposure time during image capturing through control of the electronic shutter by this CCD drive circuit 22.

On the other hand, a CDS (Correlated Double Sampling)/AGC (Automatic Gain Control) 24 is provided after the CCD 20 and this CDS/AGC 24 applies correlated double sampling to the output signal of the CCD 20 and performs predetermined amplification processing as well. This CDS/AGC 24 is provided with a DSP (Digital Signal Processor) 26 via an A/D converter 25. This DSP 26 applies various kinds of processing such as white balance, gamma correction, etc., forms, for example, a brightness signal and color-difference signal and performs photometric processing to control brightness.

Furthermore, a microcomputer 28 that performs various kinds of overall control over the above-described circuits is provided and this microcomputer 28 also controls a light source apparatus and various circuits in the processor, too. Furthermore, the processor is provided with a signal processing circuit 30 to input an image signal output from the DSP 26 and a D/A converter 31 and the signal processing circuit 30 performs various kinds of processing to output the image signal to the monitor.

Figure 2:
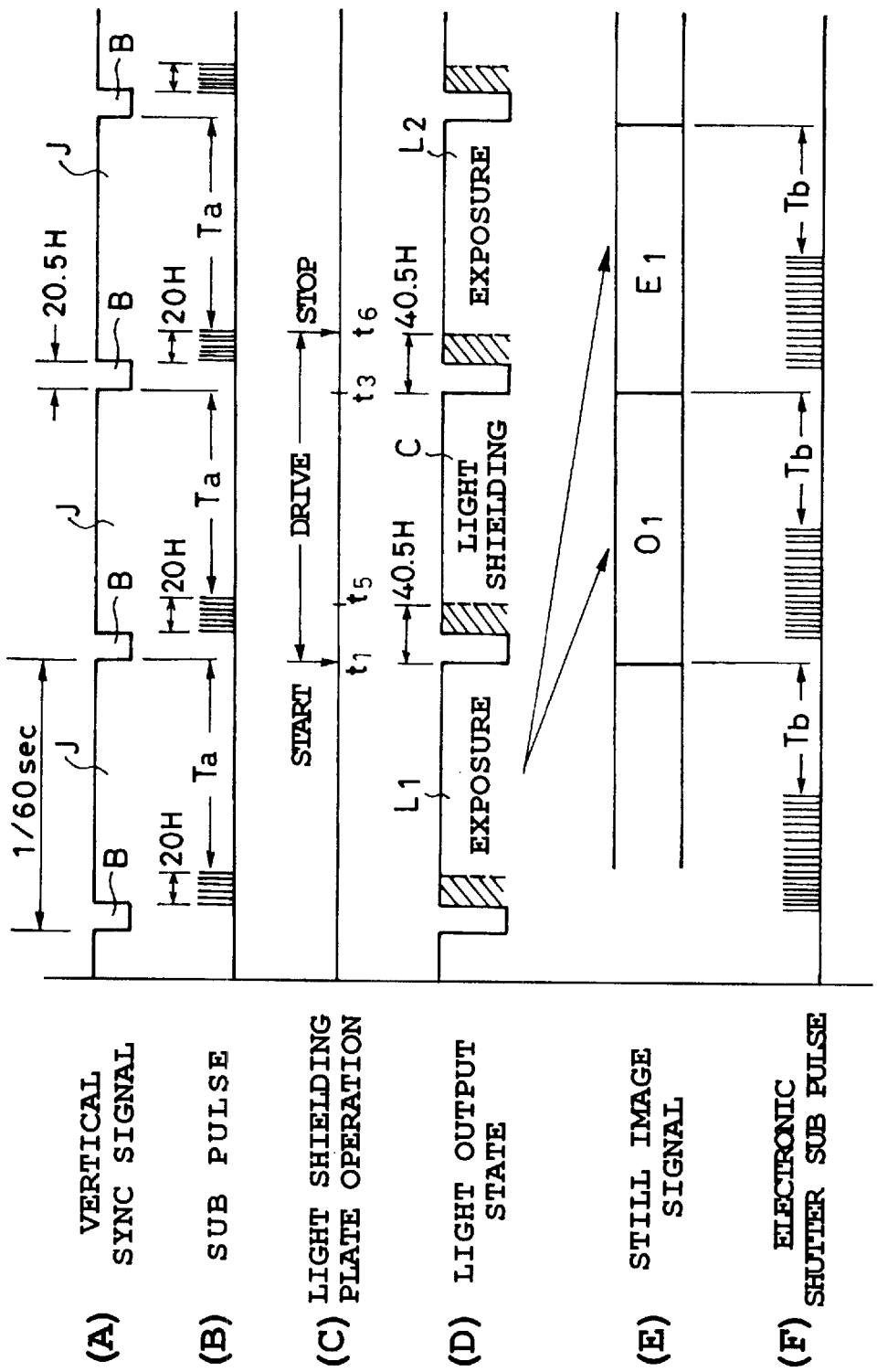
FIGS. 2(A) to 2(F) illustrate waveform charts showing operations or actions of various sections when a light shielding plate of this embodiment is driven.

This embodiment has a configuration as shown above and its operation will be explained with reference to FIG. 2. As shown in FIG. 2(A), this embodiment uses a vertical sync signal having a 1/60 sec period and the CCD drive circuit 22 forms discharging pulses (SUB pulses) in FIG. 2(B) to provide a non-operating period. That is, the CCD drive circuit 22 forms, for example, 20 SUB pulses at timing of 1H (H: horizontal scanning period) in the start part of an effective period J of the vertical scanning period and creates a 20H non-operating period (this period can be set arbitrarily) after the 20.5H blanking period B. In this way, the maximum exposure time at the CCD 20 becomes Ta.

First, when a moving image is formed, the light shielding plate 14 in FIG. 1 is placed in a position where the light shielding plate 14 does not block the light from the lamp 11 as shown in FIG. 4(A) and this lamp light is irradiated onto the object through the light guide 16. An image of the object illuminated in this way is captured by the CCD 20 and a 1-frame moving image is formed by reading the charge stored in this CCD 20 during the time Ta in field units (e.g., pixel mixed reading system). That is, the field signal output from this CCD 20 is subjected to color image processing through the CDS/AGC circuit 24, DSP 26 and signal processing circuit 30, etc., then supplied to the monitor and in this way a moving image of the object is displayed on the monitor.

On the other hand, when a freeze switch provided at the scope operation section is operated, the microcomputer 28 outputs a command to drive the light shielding plate 14 to form a still image to the light shielding plate drive circuit 18. This light shielding plate drive circuit 18 rotates the light shielding plate 14 a turn between the start point ti and stop point $t_6$ as shown in FIG. 2(C) and thereby shields light for a period C next to an exposure of $L_1$ (time Ta) as shown in the light output of FIG. 2(D).

That is, as shown in FIG. 2(C), control over the start time of the light shielding plate 14 is performed during a 40.5H period of $t_1$ to $t_5$ which corresponds to the blanking period B (20.5H) plus the non-operating period (20H) to set a condition in which the light from the lamp 11 is completely shielded. Furthermore, control over the stop time of the light shielding plate 14 is performed during a 40.5H period of $t_3$ to $t_6$ which corresponds to the blanking period B plus the non-operating period to set a condition in which the light from the light source is output from the light-shielded condition. Here, the periods $t_1$ to $t_5$ and $t_3$ to $t_6$ are longer than those of the conventional art by 20H (approximately 1.27 msec) and has an advantage of giving an adequate margin of time for control over the starting and stopping times by that much.

Then, reading pulses are used for all pixel signals of exposure $L_1$ during time Ta shown in FIG. 2(D), and as shown in FIG. 2(E), an odd field signal $O_1$ is read for the next light shielding period C and an even field signal $E_1$ is read for the next period (vertical scanning period). A 1-frame still image signal composed of these field signals $O_1$ and $E_1$ is subjected to processing similar to that of a moving image and then supplied to the monitor and as a result, a still image of the object is displayed on the monitor.

Furthermore, the light source apparatus of such an electronic endoscope apparatus controls the amount of aperture of the light quantity adjuster 12 based on a photometric signal obtained from the DSP 26 and in this way controls the brightness of the image. It is also possible to control the brightness of the image through electronic shutter control by the CCD drive circuit 22. That is, in this case, as shown in FIG. 2(F), after the 20H non-operating period, it is possible to set the exposure time to Tb in the figure by forming electronic shutter SUB pulses by the CCD drive circuit 22 and discharging the stored charge and changing this exposure time based on the photometric signal allows the brightness of the image to be kept constant.

As explained above, the present invention has the effects of allowing control over the light shielding plate at the starting and stopping times with an adequate margin of time, making it easier to drive the light shielding plate with a simple circuit configuration.

What is claimed is:

1. An electronic endoscope apparatus that drives a light shielding plate, comprising:

an image pickup element that captures an image of an object under observation illuminated by light source light;

a light shielding plate that shields said light source light for a predetermined period to read all pixel signals obtained by this image pickup element;

an image pickup element drive circuit that sets a non-operating period so that charge stored by said image pickup element is discharged during a predetermined period within an effective period following a blanking period of a vertical scanning period and reads and controls the charge stored in the effective period except this non-operating period as image pickup signals; and a light shielding plate drive circuit that performs drive control over said light shielding plate during a period including the non-operating period set by this image pickup element drive circuit.

2. The electronic endoscope apparatus according to claim 1, wherein when a moving image is formed, the charge stored is read from said image pickup element every 1 vertical scanning period as field signals without driving said light shielding plate and, when a still image is formed, said light shielding plate is driven and the charge of all pixels stored through exposure within a 1 vertical scanning period is read as frame signals.

3. The electronic endoscope apparatus according to claim 1, wherein electronic shutter control is performed for adjusting a time of discharging the stored charge following the control of said non-operating period to thereby control an exposure time.

* * * * *